United States Patent [19]

Morris et al.

[11] 4,041,774
[45] Aug. 16, 1977

[54] ACOUSTIC DATA ACQUISITION DEVICE

[75] Inventors: Winfred L. Morris; Donald O. Thompson, both of Thousand Oaks, Calif.

[73] Assignee: Rockwell International Corporation, El Segundo, Calif.

[21] Appl. No.: 702,254

[22] Filed: July 2, 1976

[51] Int. Cl.² ............................................. G01N 29/00
[52] U.S. Cl. ..................................................... 73/67.9
[58] Field of Search ............ 73/67.8 R, 67.8 S, 67.9, 73/67.7; 235/151.3

[56] References Cited

U.S. PATENT DOCUMENTS

| | | | |
|---|---|---|---|
| 3,857,052 | 12/1974 | Beller | 73/67.8 S X |
| 3,942,358 | 3/1976 | Pies | 73/67.8 S X |

Primary Examiner—Jerry W. Myracle
Attorney, Agent, or Firm—L. Lee Humphries; Craig O. Main

[57] ABSTRACT

Acoustic signals are received, selectively filtered, and digitally processed, e.g., by digitizing an amplitude, the peak of an echo, or the transit time, and the digital data are stored in a memory whose storage cells are associated with particular frequencies. Other acoustical signals are similarly processed but compared with the reference data to obtain a spectral representation of differences or ratios.

29 Claims, 7 Drawing Figures

ACOUSTIC DATA ACQUISITION DEVICE

BACKGROUND OF THE INVENTION

The present invention relates to increasing the detection sensitivity for defects or other specific features in a structural material using ultrasonics.

Ultrasonics is used increasingly for nondestructively testing and inspecting parts of structural material for detecting defects, flaws, etc., in its interior. Ultrasonic echo sounding is actually a tool of long standing. Successful practicing of this method has raised hopes for broadening its use. Specifically, one does not merely wish to detect the relative timing of a return echo or the absorption of a penetrating ultrasonic wave or beam; rather it is deemed desirable to make full use of the fact that the interaction of an ultrasonic signal with the texture of the material in the general sense is quite complex, and the signals being received carry with them the complexity of that interaction.

One major aspect of interest is that the interaction of acoustic waves with the material is usually frequency selective, or to say it differently, properties of a structural material which affect in one way or another acoustic vibrations have dispersive characteristics or are frequency dependent otherwise. Of course, the resolution of a flaw detecting method using ultrasonic echo signals is inherently frequency selective due to diffraction. Diffraction, however, is a phenomenon which, at least in the first order, is quite independent of the propagative medium and of the type of waves used. The situation is quite different as regards dispersion and frequency dependency of absorption as these phenomenon are to a considerable extent dependent upon the type of material, its internal texture thermal state, etc., and each instance is uniquely related to the type of waves used, for example, elastic vibrations. In conjunction therewith, a significant problem arises from the frequency dependency of transduction that is to say neither the generation nor the immediate transmission, nor the reception of acoustic signals is constant with frequency. On the other hand, employment of broad banded signals is desirable for reasons of resolution, detection of dispersion, etc.

DESCRIPTION OF THE INVENTION

It is an object of the present invention to provide a new and improved apparatus for analyzing the frequency selective dependency and sensitivity of ultrasonic signals as received.

It is another object of the present invention to provide a new and improved apparatus for eliminating frequency dependency of the equipment used for ultrasonic testing and inspection of structural material.

It is a further object of the present invention to provide a new and improved apparatus for determining dispersive and other frequency dependent properties of and in structural materials using ultrasonics.

It is a specific object of the present invention to provide a new and improved apparatus for the generation of a representation of spectrum signatures of broad banded elastic vibrations as detected.

In accordance with the preferred embodiment of the present invention, it is suggested to analog process an acoustic signal as received following interaction with a part of structural material and to extract narrow banded components from the broad banded signal. Digital information is extracted from each of the narrow banded signal components either by digitizing an instantaneous amplitude, or by digitizing a relative or absolute peak value, or by metering the relative time of arrival of a particular signal portion, for example, the peak of an echo. That digital information is referenced to a reference spectrum being stored digitally in a memory, and the result is displayed or plotted for inspection.

The reference spectrum has preferably been obtained with the same equipment and, for example, in conjunction with a reference sample of similar structural material or in conjunction with the same material or even with the same part when in a particular physical state (temperature, stress, etc.), or in conjunction with a medium known to have propagative properties for elastic waves which are not frequency dependent. A major purpose here of generating the reference spectrum is to incorporate therein the effect of frequency dependent properties of the equipment as used while, for example, the material being acoustically probed for obtaining the reference spectrum has known properties or is of known uniformity. The reference date may represent particular dispersive properties or particular spectral distribution of amplitudes, and subsequent tests involving the same material have the purpose of (a) finding relative differences in different locations of the same sample or specimen, or of (b) finding changes in time of these properties.

The acoustic signals may be generated in a suitable fashion, for example, by way of an energizing pulse source cooperating with a transmitter/receiver causing a broad band ultrasonic signal to propagate through the material. The pickup may include detection of back scatter or other echos. Alternatively, the pickup may be separated from the transmitter for detecting straight through bulk waves, surface waves, Lamb waves, or the like.

For each ultrasonic energizing pulse as transmitted, one component of a norrow band of frequencies is extracted, and in order to obtain the desired spectrum distribution additional pulses are needed, produced, and launched while the frequency selectivity of the detection and processing operation is changed. In all these cases, the reference data as well as the subsequently acquired raw information data can be regarded as signatures being indicative of frequency dependent properties represented on the basis of a spectrum.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 illustrates a sample or part 1 of structural material to be inspected or to serve as a reference sample, or both. The inspection is to be carried out by means of ultrasonics and a transducer 10 is provided accordingly. The transducer may be of the transmit/receive variety, for example, a piezoelectric transducer which can be coupled acoustically to the sample for transmitting thereto an acoustic signal and for receiving shortly thereafter any echo, either from a flaw therein, or from the back boundary of the object 1.

Figure 1:
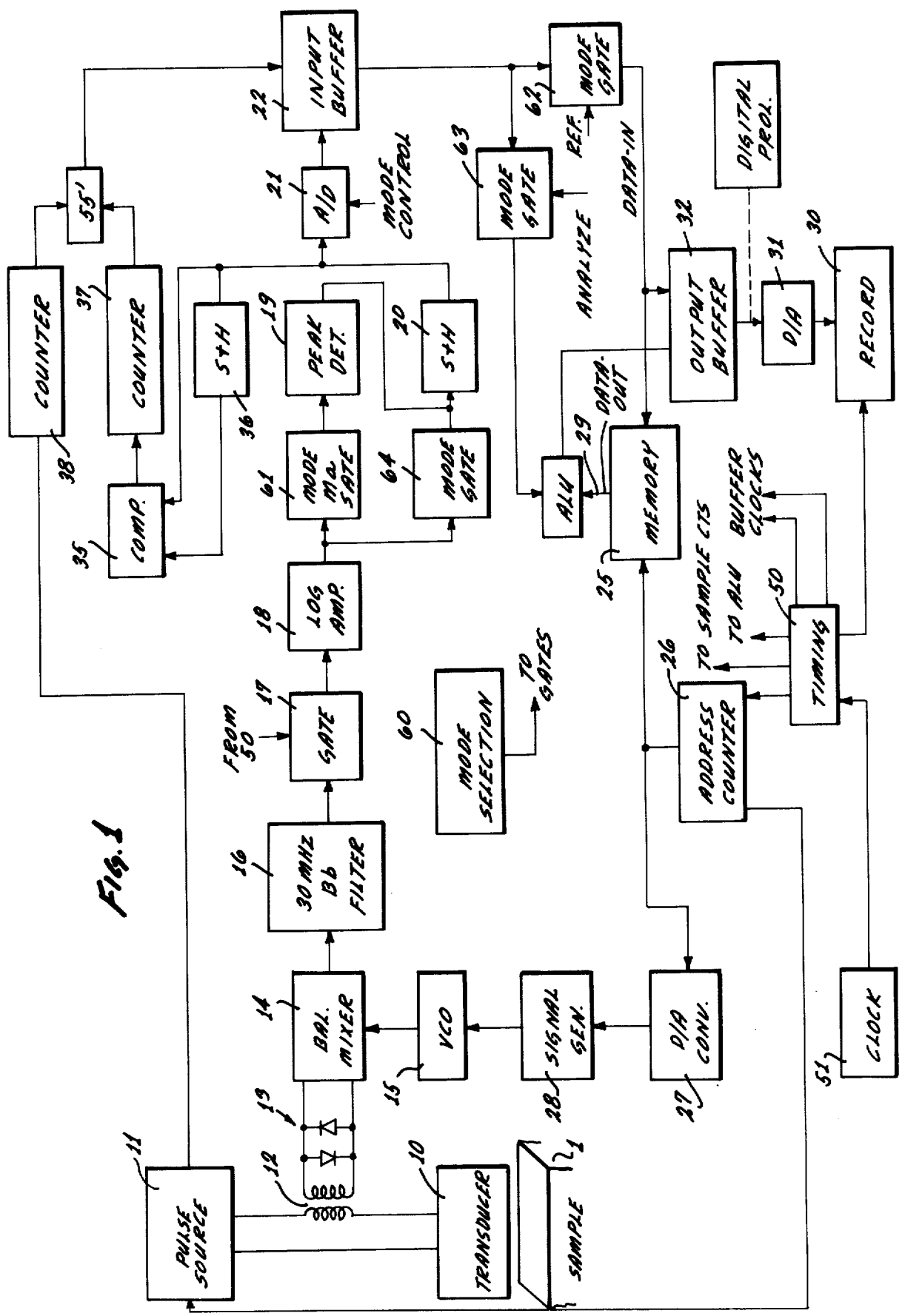
FIG. 1 is a block diagram of a system incorporating the invention features of the preferred embodiment.

The transducer 10 is driven by a pulse source 11 of conventional design using a broad banded pulse of well defined shape in response to a trigger signal. The trigger signal is issued by a timing circuit 50 to be described more fully below. Since transducer 10 is to be of the input-output variety, any return signal will be developed as an electric signal that is effective across the connection between the two devices 10 and 11. In order to extract that echo signal, this connecting circuit includes a broad band, high frequency transformer 12.

The secondary circuit of transformer 12 is shunted by a pair of diodes 13 to limit the amplitude of any signal that enters the receiver. The signal levels are chosen so that diodes 13 pass any echo signal at uniformly low impedance and the limiting function is not effective for this information signal. However, the initial pulse from source 11 has significantly greater amplitude and is, therefore, severely limited by the diodes. This is important as the full amplitude of that initial pulse should not be transmitted to the pickup circuit to be described and the diodes 13 are effective for that purpose.

The transformer secondary is connected to a balanced mixer 14 of known construction receiving, in addition, the output of a VCO 15. The mixer 14 generates signals which include the sum and the difference frequencies of respective input signals. Presently, only the difference signal is to be used. As will be explained shortly, the VCO 15 will be adjusted to provide a frequency within the range from about 30 MHz to about 40 MHz. The particular frequency as so provided by VCO 15 is beat with the broad range of frequencies transmitted by transformer 12. The output of mixer 14 is passed through a narrow band pass filter 16 with a center frequency of 30 MHz so that only one narrow banded range is selected by this filtering.

Let the VCO output be 30 MHz + $f$, then the difference signal from the band pass filter 16 is $(30 + f) - f$, whereby the subtracted component carries all the characteristics of the echo component having that particular frequency $f$. Thus, the difference signal of 30 MHz will have the same characteristic features.

As VCO 15 is adjusted to particular but different values ranging, for example, from 31 to 40 MHz, the echo signal component selected therewith has a frequency from 1 to 10 MHz and their respective characteristic features are, in each instance, included in the signal that passes filter 16. Thus, the devices 14, 15, and 16, together constitute a variable frequency selective means which analog processes the echo (or other detected ultrasonic signals to extract or separate therefrom a narrow banded component of the selected frequency.

The 30 MHz filtered mixer signal is applied to a gate 17 which is open for a limited period of time only to suppress noise and to supress particularly the main driver pulse. That gate 17 could actually be placed anywhere in the signal path 12, 13, 14, and 16. However, in either case, gate 17 establishes a time gated looking window in which the information of interest is to occur.

The output signal permitted to pass gate 17 is amplified in a logarithmic amplifier 18 so as to reduce the dynamic scale range. Conveniently, we shall at first continue to describe a mode of operation which can be described briefly as "peak-reference" mode. However, the analog signal processing up to amplification in stage 18 is mode independent.

The system as a whole may be under control of a mode selector 60 which is a dial, a set of switches or the like, responding, for example, to manual selection of the desired operational mode. The peak-reference mode is characterized by sampling the peak amplitude of each echo signal at the selected frequency for use as a single frequency reference. Presently, a gate 61 is opened by the selector circuit 60 and upon selection of the peak reference mode, so that the output of amplifier 18 is applied to a peak detector 19. Concurrently with opening the window the peak detector is zeroed or set to a fixed but small signal level to avoid response to noise. Sometime after the echo must have arrived, if it has occurred at all, the timing unit 50 issues a signal to a sample-and-hold circuit 20. The timing of that sample pulse may also be determined by mode selector 60. Conceivably, the sampling pulse is timed in relation to the looking period of opening gate 17, and may occur at the conclusion of that window.

The output of circuit 20 is applied to an analog-to-digital converter 21 which, in turn, feeds a buffer 22. It can also be said that the elements 19 to 22 extract a particular digital information from the analog signal component output, having the selected, narrow band frequency. In this particular case the particular digital information is the digitized peak amplitude value on a logarithmic scale.

The clocking input for buffer 22 may also be derived from the timing unit 50 whereby particularly the buffer clock may always occur at a particular delay following the sampling pulse of circuit 20. For the sake of convenience, it is presumed that element 21 is a parallel operating A-to-D converter, but for economic reasons, a series converter may well suffice. In that case, a series of clocking pulses is derived from timing unit 50 following the settling of the output at sample circuit 20.

The buffer 22 is actually the input register for a memory 25. The memory 25 is of the read-write variety, and may be a core memory of known construction. In the general sense, it may be of the random access type, but it suffices here to incorporate the addressing and access function with the function of a counter 26 so that always one particular location in the memory is accessed, and that location is defined by the count state of counter 26. Providing for a true random access capability to memory 25 would be necessary only if it were desirable to access any location in the memory in a random fashion. That may be an optional feature but is not essential for the principle purpose of practicing the invention, namely, to generate data for spectrum analysis in the general sense which task inherently requires an orderly presentation of data in association with different frequencies, and that order is established here by correlating the sequence of memory addresses with a sequence of frequencies.

Each memory location may have eight locations to the bit level (byte size memory) and the memory may have a capacity of 32 words or a total bit capacity of 256. Consequently, the counter 26 is able to count from 0 to 31 and recycles at count state 32. However, it may be desirable to halt the counter at count state 31 and to require some external starting pulse or command for recycling because a run covering the desired spectrum range has now been completed. Also, when the counter 26 has reached recycling condition, it may be desirable to halt the operation because a new run may require some operator intervention.

As stated above, we presently describe the peak-reference mode pursuant to which reference values are generated and stored. Hence, mode gate 62 passes the content of the buffer 22 to the respective memory address as accessed by counter 26 in that instance. As far as the mode control is concerned, the peak reference mode when selected and established by selector 60, will cause the memory 25 to operate in the write mode. The link between buffer 22 and memory 25 but beyond the gate 62 may actually constitute the date-in bus for the memory. Again, it should be said that for economic reasons the data transfer may be a serial one but, of course, a parallel transfer is faster.

Having stored the content of buffer 22 in the addressed memory cell, this particular acquisition cycle is completed, but the run covering the entire range of frequencies of interest is continued by closing a loop which is established as follows.

The count state of counter 26 is also applied to a digital-to-analog converter 27 (which is again a mode independent operation, just as the sampling process up to amplifier 18) and the output of the converter 27 is processed in circuit 28 which can also be described as a VCO-bias circuit; it converts the output of the converter 27 into a suitable signal for the control of the VCO 15. Thus, the counter 26 determines also the frequency to be selected by the filtering process. Of course, the fact that the system establishes therewith a number association between selected frequency and address number is incidental, and merely convenient. However, association between a particular memory address and location, and a frequency is an important feature for implementing the invention.

The entire circuit is under the control of a clock 51 which is the primary input for the timer and sequencer 50. Timer 50 includes a counter which counts the clock pulses, and it further includes internal gating circuitry to provide control and sample pulses of predetermined or predeterminable periods and for predetermined or predeterminable periods. This counter in unit 50 recycles particularly at a particular count state for starting a new sampling cycle. The recycling rate of the counter in the timing unit 50 determines the acquisition and sampling rate. A full cycle of the timing unit 50, therefore, is associated with the acquisition of a particular information detail pertaining to one selected frequency component. Such a full cycle is in each instance associated with one count state of counter 26, and in the mode presently described, the particular information acquired during one sampling cycle is stored in the, thus, accessed memory location.

Upon (or following) recycling the counter unit 50 issues a start pulse into address counter 26 which (a) advances the address counter 26 for accessing the next location of memory 25 and (b) triggers the pulse source 11 to issue a pulse or signal for transmission to transducer 10 which, in turn, enables an acoustic signal. Gate 17 is closed at that time but will be opened by another timing signal from sequencer 50 and at a delay which is (a) shorter than the delay leading up to the arrival of an expected echo, but (b) longer than any ringing and any other transient phenomena in the circuit 12, 13, 14, etc. This particular delay may be adjustable and since clock 51 is relatively fast, the length of the window covers several sequential states of the counter in sequencer 50 to keep that window (gate 17) open for the necessary period of time so that one is certain that the expected information will, in fact, appear during the gating-open period.

In the meantime, the new count state of counter 26 has been applied to the D/A converter 27 which caused circuit 28 to set the VCO 15 so as to generate a frequency which is 30 MHz plus the next frequency to be sampled during this next sample cycle. Mixer 14 is ready to beat the soon expected echo signal with the VCO output frequency.

As soon as the echo appears, mixer 14 forms the difference frequency so that the particular signal having the selected frequency, appears as the 30 MHz signal at the output of filter 16 and passes through the now open gate 17; amplifier 18 contracts the amplitude scale, and peak detector 19 probes the particular signal as to its highest amplitude, and applies it to the sample and hold circuit 20. The sample and hold circuit 20 is actuated by another timing signal from sequencer 50, which, as was stated above, may be the clock pulse that closes the gating window (gate 17). Following sampling, the detected peak amplitude is digitized in 21 and stored in buffer 22. Gate 62 is open during this mode, and the data thus acquired are read into the previous opened memory location. The memory input clock and timing signal is, in fact, the last one of this particular cycle and shortly thereafter timer and sequencer 50 recycles. The timing of recycling, of course, depends upon whether or not the various digital operations are parallel operations, if they are serial operations they require a certain number of clock pulses for passing information from one facility to another. As the counter in timer 50 recycles the counter 26 is advanced to the next state for (a) updatiang the VCO output, to furnish the next frequency, (b) opening the next memory cell, and (c) launching the next transducer pulse. The operation then continues as before.

In addition, the data which have been read into memory may have been applied to an output buffer 32, converted into an analog signal in a stage 31 and recorded on or displayed by a suitable output device 30. Device 30 may be a CRT, a plotter or the like. Conceivably, the time axis of recorder 30 may be tied to the sequence of number changes in counter 26 because the counter 26 runs actually through a representation of the entire frequency spectrum being covered. However, open loop synchronism between plotter or CRT operation and the rate of covering the frequency range of interest by successive sampling cycles may well suffice. On the other hand, recycling and halting of counter 26 at the end of a run may be tied to the retrace of the plotter of device 30. As was stated above, the sequence of sampling cycles continues and after 32 samples have been taken, counter 26 may recycle and/or halt. Now, 32 samples have been stored in memory and are available as reference for further processing.

Figure 2:
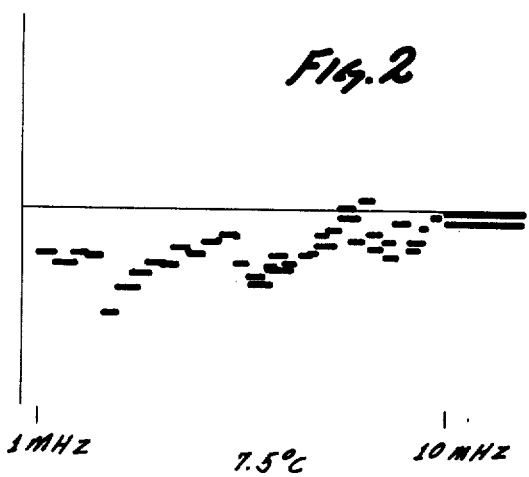
FIG. 2 is a graph showing reference data acquired by and stored in a system as shown in FIG. 1; the graph exhibits specifically logarithmic amplitude versus frequency.

FIG. 2 is a representative example of a complete plot showing a complete run covering the entire frequency range of interest. The figure shows in particular the peak amplitude of echo signal components plotted against frequency of a structural material, at, for example, 7.5° Centigrade.

It may now be of interest to determine any change in the propagative or reflective properties of the structural material 1 under investigation. Or it may be desirable to determine any difference such property exhibits in another part. Generally, it may be desirable to determine any change of the property in time and/or as to location. Whenever that determination is to be made, another run is begun, but first the mode has to be changed.

The mode now to be described could be termed "peak-analize" mode. The operation proceeds identically with the previous mode as far as the frequency selection and filtering is concerned. Also, gate 61 is open for this particular mode and the quantized raw data are set into buffer 22. Now, however, gate 62 is blocked and a gate 63 is opened. In addition, the memory 25 is operated in the read mode so that the content of any accessed location is fed to the output bus 29 of the memory. In other words, the mode change involves primarily the operation of the memory to switch from write operations to read operations.

The output of gate 62 is applied to one side of an adder, identified in FIG. 1 as block ALU which could be an arithmetic-logic-unit. The other side of adder ALU is connected to the output bus 29 of the memory. Unit ALU substracts the two bytes from each other and feeds them to the output buffer 32.

It should be mentioned that unit ALU could be constructed as a parallel adder operating in the subtract mode, but for economic reasons, a serial adder operating in the subtract mode may suffice, in which case the memory output buffer (not shown) and the buffer 22 may be operated by a high-speed clock for serial readout as was briefly mentioned earlier. Also, in this case the timer 50 will provide the needed shift clock pulses operating at the rate of clock 51. Buffer 32 could then be used as an assembly buffer with serial input. Additionally, a serial read-out of buffer 32 in conjunction with a serially operating converter 31 may be desirable for economic reasons.

Figure 3:
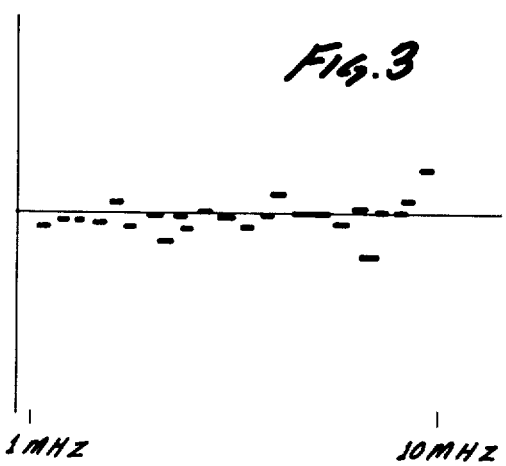
FIG. 3 is a similar graph showing digitally processed data using the reference signatures as per FIG. 2.

In any event, the recorder 30 now plots and/or displays the differences between the currently acquired samples and the reference samples and in dependence upon frequency. The plot may appear as shown in FIG. 3. For this specific example it has been assumed that the same sample location was used that generated the reference spectrum of FIG. 2, but the temperature was raised to 47° Centigrade. Therefore, this particular plot permits study of the frequency dependency on temperature of the absorptive qualities of the material in question. Such a diagram may be of interest not just for purposes of flaw and defect detection, but it may be of interest per se as regards particular properties of the material.

It should be mentioned that sub-modes of the operation may be provided in that in one sub-mode one subtracts the reference data from analysis values, and in the other sub-mode, the unit ALU forms the difference: analysis values minus reference values. Since all data have passed through the logarithmic amplifier originally, the formed difference is really the logarithm of the respective ratios. Scale expansion or logarithmic scaling in recorder 30 may permit the direct display or recording of the respective ratios. In FIGS. 2 and 3 one vertical scale unit is the equivalent of 5.5 db.

In order to provide the system with greater versatility, memory 25 should be exchangeable in that, for example, a particular memory with stored reference data can be unplugged and replaced by an empty array of memory cells of like format. Alternatively, memory 25 may actually consist of several such 32-byte-size units which are selected individually upon selection of a different mode by operation of device 60.

It may now be assumed that the system can operate in a mode which could be termed "amplitude-reference" mode. As far as the reference aspect of this mode is concerned, gate 62 will be open and gate 63 will be closed, so that the data as acquired will be stored in memory as described. The cyclic updating of the selected frequency through control of VCO 15, and updating of counter 26 is the same as described, so is the analog signal processing up to amplification 18. However, a gate 64 is open while gate 61 is closed. The sample-and-hold circuit 20 is operated by timer 50 at a fixed delay, following, for example, the initial energization pulse. Thus, in this case, the echo signal is sampled not for its peak amplitude at the selected frequency, but as to its value a particlar delay following emission of the probing acoustic wave.

The resulting amplitude is digitized, passed through buffer 22, and stored in memory as described. The correlative mode can be termed "amplitude-analyze". In this particular mode gates 64 and 63 are open, and the data acquired are compared with the stored references. The difference (or ratio) is plotted or displayed on and by device 30.

Figure 5:
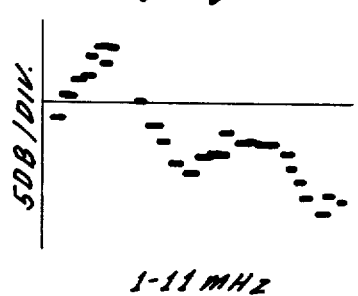
FIG. 5 is a graph similar to FIG. 3 showing a reference amplitude versus frequency spectrum.
Figure 4:
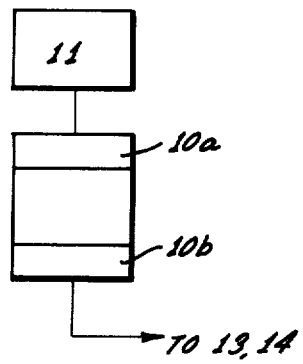
FIG. 4 shows a modification of a portion of the system as shown in FIG. 1 for adapting it for measuring transmission through a specimen from one surface to an oppositely located surface.

FIG. 5 is a plotted graph representing reference data of such sampled amplitudes. The arrangement, however, was changed here in that transmitting and receiving transducers were separate units and placed on opposite ends of a path to be investigated as to transmission. FIG. 4 shows that modification wherein, 10a is a transmitting transducer operated by pulse source 11 as before, and 10b is a pickup transducer feeding the signals as received from the sample path between transmitter 10a and pickup 10b to the same signal processng circuit as described with reference to FIG. 1.

In this case, then, the reference data is produced primarily to eliminate the frequency dependency of the transducers. The sample was a simple water bath known to have little frequency dependency as to transmission and absorption of ultrasonic waves, for example, 1 to 11 MHz.

Figure 6:
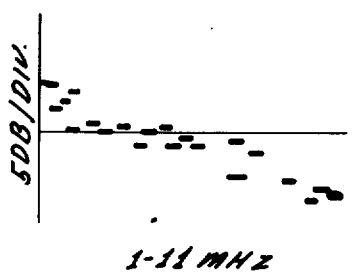
FIG. 6 is a similar type of graph but representing processed data.

FIG. 6 shows a plotted graph in which the same transducer assembly was used, but the sample path between the transmitting and pickup transducers was constituted of water and a fiber reinforced composite. The figure represents specifically the spectrum of the received amplitude signals as sampled in dependence upon frequency from which the effect of the frequency dependency of the transducers has been eliminated by virtue of the reference data as per FIG. 5 and through processing in a manner described above.

Another mode, or better, a pair of modes, could be termed "delay-reference" and "delay-analyze". These modes differ from each other in a manner as described, in that the first mode is provided for acquiring reference data on the dispersive properties of the material. In the second mode, current data on dispersion are acquired in like fashion and compared with the stored reference values. The particular values of interest are the periods of time which elapse between the issuance of the pulse from source 11 and the appearance of the highest echo peak at the selected frequency.

The echo signal as received, is analog-processed along the path 12-18 as described. Also, mode gate 61 is open, but the analog-to-digital converter 21 is disabled. The sample and hold circuit 20 is operated for this mode by the high speed clock 51 directly, and the train of sampled outputs is set in steps to a second sample-and-hold circuit 36 and at the resepctive next clock. The output of circuit 36 and the current output of sample and hold circuit 20 are applied to a comparator 35 which thus compares the current sample with the previous sample. The comparator, for example, may be disabled for the other modes previously described.

If the comparator finds that the current sample is higher than the previous sample, a counter 37 is reset to start counting anew. This counter is also operated by a high speed clock, or even by a higher one. Thus, the running count state of counter 37 is indicative of the time that has elapsed from the respective previously highest sampled value which will be the peak of the echo if the counter 37 is not reset thereafter within a reasonable period of time. Another counter 38 runs concurrently with counter 37, but counter 38 is started, i.e., reset, by the transducer pulse. Hence, the difference in count states of counters 38 and 37 is indicative of the delay or transit period from the time of occurrance of the transducer output to the time of receiving a signal such as a returned echo peak and at the particular frequency under investigation.

As indicated by reference number 55', the same adder that is being used for subtracting raw data from reference signatures, can be used also here on a time sharing basis, and to subtract the count numbers in counters 38 and 37 from each other. The difference is set into the buffer 22. The difference-forming operation is triggered by a timing signal from sequencer 50 which issues a particular signal when a peak, if any, must have occurred with certainty.

As was mentioned above, these signals representing peak delay are stored in memory as reference in the one mode, and subsequently delays measured in like fashion are compared with the stored references in the other mode. The circuit can be modified by triggering a counter such as 38 from a constant point in time derived, e.g., from timing circuit 50, while counter 37 is operated as described except that counter 37 always runs a full count, i.e., it meters a fixed period following detection of an echo peak. As counter 37 has completed its fixed count, it stops counter 38.

Counter 38 now holds a count number which is the sum of two numbers. The first one represents the time from the arbitrary zero point to the detection of the echo peak, and the second number represents the fixed delay for counter 37 to complete a count. That number may be adjustable and it represents the uncertainty as to when the echo peak can be detected as distinguished from other peaks.

Figure 7:
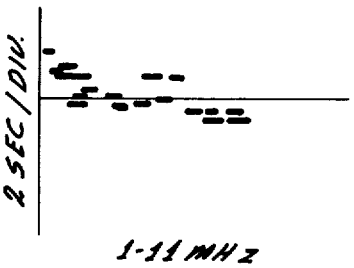
FIG. 7 is a graph illustrating dispersive properties.

The content of counter 38 is used directly as reference representation of echo timing. It should be noted that subsequent runs carried out in like fashion will yield analogous timing data, and the difference between these data and the stored reference data are directly indicative of differences in echo timing in dependence upon frequency. FIG. 7 illustrates the time of arrival of different peaks of surface waves propagating over layered material. This dispersive spectrum can be used as reference to monitor, for example, how the propagation periods vary with time.

The invention is not limited to the embodiments described above but all changes and modifications thereof not constituting departures from the spirit and scope of the invention are intended to be included.

We claim:

1. Apparatus for acquiring information on acoustic properties of structural materials, comprising:
    means for receiving an acoustic signal from a part of such a material;
    means for processing the signal frequency-selectively for extracting therefrom narrow banded components having different frequencies;
    means for extracting digital information from said narrow banded components;
    means for storing digital reference information means for digitally processing the extracted digital information with the stored reference information; and
    means for providing a representation of the processed information in dependence upon frequency.

2. Apparatus as in claim 1, wherein the means for extracting includes peak detection means for detecting a peak value of said component signal; and means for digitizing the peak value.

3. Apparatus as in claim 1, wherein the means for extracting includes amplitude detector means and means for digitizing the detected amplitude.

4. Apparatus as in claim 1, wherein the means for extracting includes peak detecting means and means for metering the time of occurrence of the detected peak.

5. Apparatus as in claim 4, wherein the means for metering operates in response to a launched acoustic signal.

6. Apparatus as in claim 1, including means for generating the reference information, the means for generating including the means for receiving, the means for processing and the means for extracting, to obtain particular narrow banded component signals as said references, the apparatus further including means for passing said latter component signals as said reference signals to said means for storing.

7. Apparatus as in claim 1, wherein said means for processing includes a logarithmic amplifier, the means for digitally processing including digital, arithmetic subtracting means to obtain a representation of the ratio of narrow banded component signals and said reference information.

8. Apparatus as in claim 1, wherein the means for receiving is incorporated in a means for transmitting acoustic signals, the received signals being acoustic echo signals.

9. Apparatus as in claim 1, wherein said means for processing the signal frequency-selectively includes a controlled oscillator a mixer connected to said oscillator and to said means for receiving; and a filter connected to receive the output of said mixer.

10. Apparatus for acquiring information on acoustic properties of structural material, comprising:
    means for receiving a relatively broad banded acoustic signal from a part of said material;
    means for extracting from said acoustic signal digital information on different, narrow banded portions of said signal;
    means for comparing said information with digital reference information, to obtain resulting information; and means for providing a spectrum of said resulting information.

11. Apparatus as in claim 10, wherein the reference information includes representation of frequency dependent properties of the said means for receiving.

12. Apparatus as in claim 10, wherein the reference information includes representation of an amplitude spectrum.

13. Apparatus as in claim 10 and including means for storing said reference information, said means for comparing includes, means for arithmetically processing the digital information as extracted together with said stored reference information.

14. Apparatus as in claim 10, wherein said means for extracting is operated by control means to obtain particular digital information, the apparatus including means for storing the particular information as reference information.

15. An apparatus for analyzing acoustic information resulting from interaction of acoustic signals with structural material, comprising:
   means for receiving a train of broad banded acoustic signals;
   means for analog processing the signal train as received to separate therefrom different frequency components;
   means for digitally processing the separated components to obtain a sequence of digital information constituting a first spectrum;
   means for providing digital information representing a second spectrum covering the same frequency range as the first spectrum; and
   means for processing the information of the first and second spectra for obtaining an indication of a normalized or referenced spectrum.

16. Apparatus as in claim 15, wherein said spectrum represent peak amplitudes of echo signals at the different frequency components.

17. Apparatus as in claim 15, wherein said spectra represent dispersive delays of echo signals.

18. Apparatus as in claim 15 wherein means are provided to store the first spectrum, to serve subsequently as second spectrum.

19. Apparatus as in claim 15, and including control means for determining a rate of acquisition, the control means connected to and operating means for launching acoustic test signals to be received by the means for receiving following said interaction.

20. An improvement in an apparatus for acquiring information on acoustic properties of structural materials, said apparatus including means for transmitting acoustic signals into and means for receiving acoustic signals from the material, said improvement comprising:
   an addressable memory for storing digital information representative of particularly dispersive acoustic properties;
   selective filter means for filtering from a broad banded signal narrow banded components corresponding to a frequency selection;
   means for operating the memory and the filter means for obtaining said selection and for obtaining particular access to a portion of the memory holding reference information related to the selected frequency;
   means for extracting digital information from the narrow banded component as selected by the filter means; and
   means for digitally processing the reference information held in the accessed memory portion in relation to the extracted digital information.

21. In an apparatus as in claim 20, said means for operating including an address counter for accessing the memory and a digital to analog converter for converting the counter state into a control signal, the selective filter means being operated in response to the control signal.

22. In an apparatus as in claim 21, said selective filter means including a voltage controlled oscillator operated by said control signal, a balanced mixer receiving an output of the voltage controlled oscillator and said broad banded signal for forming a difference-of-the-frequencies signal; and a narrow banded filter receiving said difference signal.

23. In an apparatus as in claim 20, said means for digitally processing including arithmetic means for arithmetically combining said reference information and said extracted digital information.

24. In an apparatus as in claim 23, said means for extracting including a logarithmic amplifier and amplitude responsive means.

25. An apparatus for analyzing acoustic information resulting from interaction of acoustic waves with structural material, comprising:
   means for transmitting a series of broad band acoustic signals into the part, the signals having similar frequency spectrum;
   means for receiving signals resulting from interaction of the transmitted signals with the material and detecting different narrow banded portions in the different signals as received, the portions differing as to frequency of the respective narrow band;
   means for extracting digital information from each of the different portions;
   a memory containing a reference spectrum in digital representation;
   means connected for digitally processing the extracted digital information in relation to the stored reference spectrum, separately for each of the different frequencies; and
   means for generating a display or recording of the spectrum of processed signals.

26. An apparatus as in claim 25, including means for stepwise changing frequency selectivity in the means for receiving and detecting corresponding to the series of transmitted signals.

27. An apparatus as in claim 25, and including means for storing extracted digital information as reference spectrum in the memory.

28. Apparatus as in claim 25, wherein said reference spectrum includes frequency dependency of operation of the means for transmitting and of the means for receiving.

29. An apparatus for analyzing acoustic signals resulting from interaction with a part of structural material, comprising:
   means for transmitting acoustic signals to the part and for receiving acoustic signals from the part;
   frequency selective means for providing a signal representing a narrow band of the acoustic signal as received subsequently to transmission of a acoustic signal;
   means for deriving digital information from said narrow band signal;

a memory holding a plurality of stored digital reference information and having significance for different frequencies;

circuit means for digitally processing the digital information representing the narrow band signal and said reference information as associated with the selected frequency to provide a related representation of the narrow band signal in relation to the reference information;

means for varying the frequency selectivity of said selective means and for changing the access to the memory for extracting therefrom correspondingly different reference information; and means for providing a representation of different ones of said relative representations as produced by said circuit means for different selected frequency and in dependence upon the frequencies as selected.

* * * * *